US008278054B2

(12) United States Patent
Jakobson

(10) Patent No.: US 8,278,054 B2
(45) Date of Patent: Oct. 2, 2012

(54) DIAGNOSIS OF METAL ALLERGY THROUGH CYTOKINE RELEASE BY T-CELLS IN VITRO

(75) Inventor: Eva Jakobson, Solna (SE)

(73) Assignee: Mabtech AB, Nacka (SE)

( * ) Notice: Subject to any disclaimer, the term of this patent is extended or adjusted under 35 U.S.C. 154(b) by 557 days.

(21) Appl. No.: 10/471,479

(22) PCT Filed: Mar. 12, 2002

(86) PCT No.: PCT/EP02/02697
§ 371 (c)(1),
(2), (4) Date: Jan. 14, 2004

(87) PCT Pub. No.: WO02/073195
PCT Pub. Date: Sep. 19, 2002

(65) Prior Publication Data
US 2004/0115744 A1 Jun. 17, 2004

(30) Foreign Application Priority Data
Mar. 12, 2001 (EP) .................................. 01302270

(51) Int. Cl.
G01N 33/53 (2006.01)
(52) U.S. Cl. ........................................................ 435/7.1
(58) Field of Classification Search .................. None
See application file for complete search history.

(56) References Cited

FOREIGN PATENT DOCUMENTS
WO WO 97/45735 A1 12/1997

OTHER PUBLICATIONS

Kuby et al. 'Immunology' W.H. Freeman and Company: New York, 2000 (p. 161).*
Minang et al. 'Nickel Elicits Concomitant and Correlated in vitro Production of Th1-, Th2-Type and Regulatory Cytokines in Subjectswith Contact Allergy to Nickel.' Scand. J. Immunol. 62:289-296, 2005.*
Rasanen et al. 'Hypersensitivity to gold in gold sodium thiomalate-induced dermatosis.' Brit. J. Dermatol. 141:683-688, 1999.*
Büdinger et al., Allergy. Feb. 2000;55(2):108-15.*
Schielen et al., J Immunol Methods. Dec. 15, 1995;188(1):33-41.*
Jakobson et al., Br J Dermatol. Sep. 2002;147(3):442-9.*
Czarnobilska et al.'Contact allergy to nickel: patch test score correlates with IL-5, but not with IFN-gamma nickel-specific secretion by peripheral blood lymphocytes.' Ann. Agric Environ Med 16:37-41, 2009.*
Spiewak et al. 'Allergic contact dermatitis to nickel: modified in vitro test protocols for better detection of allergen-specific response.' Contact Dermatitis. 56:63-69, 2007.*
Lindemann et al. 'Detection of Chromium allergy by cellular in vitro methods.' Clin. Exp. Allerg. 38:1468-1475, 2008.*
Minang et al. 'Nickel, cobalt, chromium, palladium and gold induce a mixed Th1- and Th2-type cytokine response in vitro in subjects with contact allergy to the respective metals.' Clin. Exp. Immunol. 146:417-426, 2006.*

Lisby et al. 'Nickel-induced activation of T cells in individuals with negative patch test to nickel sulphate.' Arch Dermatol Res. 291(5):247-52, 1999.*
Lisby et al. 'Nickel-induced activation of T cells in individuals with negative patch test to nickel sulphate.' Arch Dermatol Res. 291 :247-252, 1999.*
Thomas, P., et al., "In Vitro T Cell Reactivity in Nickel Allergy: Comparison of T cell Clonality, Cytokine Expression and Mediator Production", *International Archives of Allergy and Immunology*, 124:292-295 (2001).
Falsafi-Amin, H., et al., "Early DNA Synthesis and Cytokine Expression in the Nickel Activation of Peripheral Blood Mononuclear Cells in Nickel-Allergic Subjects", *International Archives of Allergy and Immunology*, 123:170-176 (2000).
Borg, L., et al., "Nickel-Induced Cytokine Production from Mononuclear Cells in Nickel-Sensitive Individuals and Controls", *Archives of Dermatological Research*, 292:285-291 (2000).
Probst, P., et al., "$T_H2$-Type Infiltrating T Cells in Nickel-Induced Contact Dermatitis", *Cellular Immunology*, 165:134-140 (1995).
Gabrielsson, et al., "Allergen-Induced Cytokine Production in IgE-Mediated Allergy", Doctoral thesis from the department of Immunology, Stockholm Univeristy, Sweden (1999).
Gabrielsson, et al., "Specific Induction of Interleukin-4-Producing Cells in Response to In Vitro Allergen Stimulation in Atopic Individuals", *Clin. Exp. Allergy*, 27:808-815 (1997).
Gabrielsson, et al., "Increased Allergen-Specific Th2 Responses In Vitro in Atopic Subjects Receiving Subclinical Allergen Challenge", *Allergy*, 52:860-865 (1997).
Gabrielsson, et al., "Increased Frequencies of Allergen-Induced Interleukin-13-Producing Cells in Atopic Individuals During the Pollen Season", *Scand. J. Immunol.*, 48:429-435 (1998).
Gabrielsson, et al., "Specific Immunotherapy Prevents Increased Levels of Allergen-Specific IL-4- and IL-13-Producing Cells During Pollen Season", *Allergy*, 56:293-300 (2001).
Gabrielsson, et al., "Influence of Atopic Heredity on IL-4-, IL-12- and IFN-γ-Producing Cells in in Vitro Activated Cord Blood Mononuclear Cells", *Clin. Exp. Immunol.*, 126:390-396 (2001).
Summer, et al., "Kinetics of In-Vitro-T-Cell Reactivity in Nickel Allergy: Analysis of T-Cell Clonality, IL-4 and IFNγ mRNA Expression Pattern (RT-PCR) and Respective Mediator Secretion", *Archives of Dermatological Research*, 293:44 (2001).

(Continued)

*Primary Examiner* — Nora Rooney
(74) *Attorney, Agent, or Firm* — Hamilton, Brook, Smith & Reynolds, P.C.

(57) ABSTRACT

An in vitro method for diagnosing a contact allergy in a subject comprises: (i) providing (a) a contact allergen; (b) T-cells from said subject; and (c) a surface to which is immobilized a first specific binding agent capable of specifically binding to a cytokine released from a T-cell in response to said allergen; (ii) contacting said sample with said allergen under conditions which are suitable for (a) release of said cytokine by T cells that have been presensitized in vivo to said allergen; and (b) binding of said cytokine to said first specific binding agent; and (iii) detecting binding of said substance to said first specific binding agent. A kit which enables the method to be carried out is also described.

23 Claims, 1 Drawing Sheet

OTHER PUBLICATIONS

Corsini, E., et al., "In Vitro Keratinocytes Responses to Chemical Allergens," *Boll. Chim. Farmaceutico*, 134:569-573 (1995).

Minang, J.T., et al., "Nickel, Cobalt, Chromium, Palladium and Gold Induce a Mixed Th1- and Th2-type Cytokine Response in vitro in Subjects with Contact Allergy to the Respective Metals," *Clin. Exp. Immunol.*, 146:417-426 (2006).

Cederbrant, K., et al., "Cytokine Production, Lymphocyte Proliferation and T-Cell Receptor Vβ Expression in Primary Peripheral Blood Mononuclear Cell Cultures from Nickel-Allergic Individuals," *Int. Arch. Allergy and Immunol.*, 132:373-379 (2003).

Lindemann, M., et al., "ELISpot: a New Tool for the Detection of Nickel Sensitization," *Clin. Exp. Allergy*, 33:992-998 (2003).

* cited by examiner

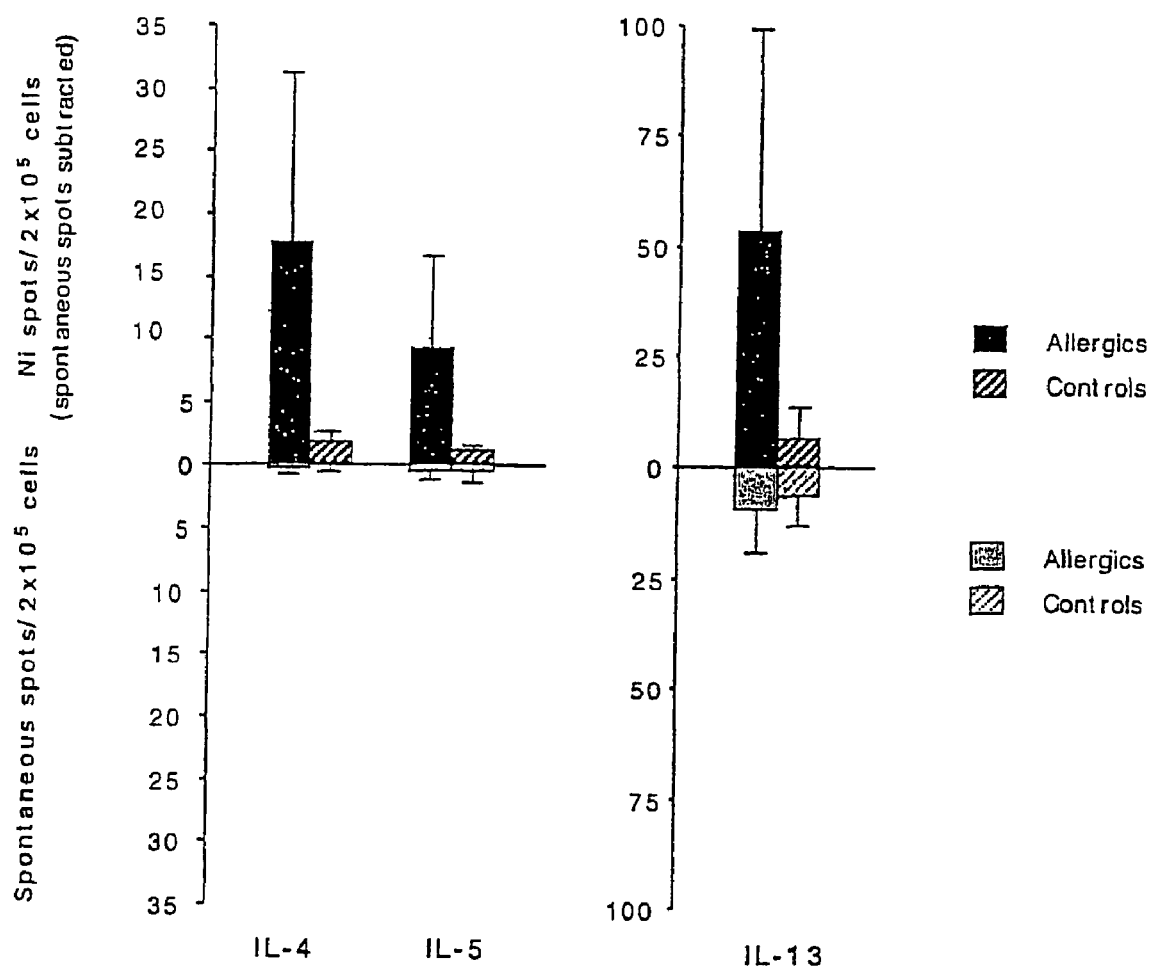

DIAGNOSIS OF METAL ALLERGY THROUGH CYTOKINE RELEASE BY T-CELLS IN VITRO

RELATED APPLICATIONS

This application is the U.S. National Phase of International Application No. PCT/EP02/02697, filed 12 Mar. 2002, published in English, which application claims priority under 35 U.S.C. §119 or 365 to European Patent Convention No. 01302270.2, filed 12 Mar. 2001. The entire teachings of the above applications are incorporated herein by reference.

FIELD OF THE INVENTION

The invention relates to a method of diagnosis of an allergy, particularly an allergy to a nickel. It also relates to a kit which can be used to carry out the diagnostic method.

BACKGROUND OF THE INVENTION

Nickel allergy is one of the most common types of contact allergies. In Europe about 10% of all women suffer from this type of allergy while being less frequent in the male population. It is an important occupational disease but due to the widespread use of nickel-containing products it is a significant problem among people in general. The difference between the sexes is partially explained by the more common use of jewellery among women and quite often ear piercing seems to be the event that induces the disease. Nickel allergy is usually life-long and there is presently no, effective treatment apart from avoiding exposure.

Unlike many other allergies (e.g. against animals, pollen, plants, etc.), contact allergies are usually not associated with a rise in allergen specific IgE antibodies. As the diagnosis of allergy in vitro is normally based on the detection of specific IgE in serum there is presently a lack of suitable serological tests for nickel allergy. The most commonly used method for establishing nickel allergy is based on the so called patch test in which nickel is introduced into the skin of the patient and, depending on the presence or absence of a local inflammation, the patent is diagnosed as being allergic or non-allergic. The measured size of the inflammatory site may also serve as an indicator of the severity of the allergy. A major drawback of the patch test, apart from the discomfort that it may cause the individual, is the risk that the exposure to nickel during the test in itself may induce or enhance the disease. The test may also give false positive or false negative responses and the capacity to respond may be affected by the hormonal status of the individual as well as by certain drugs and by uv-light.

Attempts have been made to measure the specific activation of cells after in vitro exposure with nickel. This has been done by measuring cell proliferation or the release of cytokines by the stimulated cells. However, given the low frequency of nickel-specific cells in peripheral blood, cell proliferation has often proven too insensitive and unreliable and the detection of nickel-induced cytokine production by ELISA usually requires the propagation and in vitro culturing of cells to first expand the population of responding cells. Furthermore, as shown from analysis of nickel-specific T cell clones, cytokine production is heterogenous and no single cytokine has been shown to be consistently produced by the responding cells.

SUMMARY OF THE INVENTION

The present inventors have for the first time demonstrated the possibility of detecting nickel-specific T-cells at the single cell level by detecting the production of interleukin-4 (IL-4), interleukin-5 (IL-5) and/or interleukin-13 (IL-13) in response to nickel exposure. Similar results have also been achieved with other contact allergens, i.e. non-nickel and non-metal allergens. Accordingly the present invention provides an in vitro method for diagnosing a contact allergy in a subject, which method comprises:
(i) providing
  (a) a contact allergen;
  (b) T-cells from said subject; and
  (c) a surface to which is immobilised a first specific binding agent capable of specifically binding to a cytokine released from a T-cell in response to said allergen;
(ii) contacting said sample with said allergen under conditions which are suitable for
  (a) release of said cytokine by T cells that have been presensitised in vivo to said allergen; and
  (b) binding of said cytokine to said first specific binding agent; and
(iii) detecting binding of said cytokine to said first specific binding agent.

The present invention also provides a kit for carrying out a method according to the invention, which kit comprises a contact allergen, a surface to which is immobilised a first specific binding agent capable of specifically binding to a cytokine released from a T-cell in response to said allergen and optionally a means to detect binding of said specific binding agent to said cytokine.

BRIEF DESCRIPTION OF THE DRAWINGS

FIG. 1 shows the release of cytokines from T cells from nickel allergic or non-allergic individuals in response to $NiCl_2$. PBMC from allergic (n=8) or non-allergic individuals (n=7) were stimulated with 50 μM $NiCl_2$ and the number of cells producing IL-4, IL-5 or IL-13 were measured by ELISpot. The bars above the axis display show mean responses to $NiCl_2$ in allergic and controls after subtraction of spots produced spontaneously. The bars below the axis display the spontaneous number of spots that have been subtracted and are shown using a reversed scale.

DETAILED DESCRIPTION OF THE INVENTION

The present invention provides an in vitro method for diagnosis of a contact allergy by detecting contact allergen sensitive T-cells. Such cells are detected using an assay capable of detecting the release of one or more cytokines from one or more T-cell in response to the allergen. The method for detecting contact allergen sensitive T-cells consists essentially of the following steps:
(i) providing
  (a) a contact allergen;
  (b) T-cells from said subject; and
  (c) a surface to which is immobilised a first specific binding agent capable of specifically binding to a cytokine released from a T-cell in response to said allergen;
(ii) contacting said sample with said allergen under conditions which are suitable for
  (a) release of said cytokine by T cells that have been presensitised in vivo to said allergen; and
  (b) binding of said cytokine to said first specific binding agent; and
(iii) detecting binding of said cytokine to said first specific binding agent.

Allergy

An allergy to any allergen that induces a delayed-type hypersensitivity reaction may be diagnosed using a method of the invention. Preferred allergens are non-protein or non-peptide allergens. An allergy that may be detected by a method of the invention is typically a contact allergy. In one embodiment, the contact allergy is a metal allergy. Preferably the metal is one that is commonly used in jewellery or other metal items that contact the skin such as in clothing fasteners. More preferably the metal is chromium, manganese, iron, cobalt, copper or zinc. Most preferably the allergen is nickel. In an alternative embodiment, the contact allergy is a non-metal allergy. Preferably the non-metal is one that is commonly used in health care products, glues, paints, rubber products or drugs. More preferably the non-metal is lanolin, methylchloroisothiazoline, methylisothiazolinone (Kathon CG), Balsam of Peru, epoxy resin, latex or neomycin.

Subject

The subject is generally a human but may beta domestic animal. Typically the animal is a non-human mammal, such as a cat, dog, rabbit, cow or horse. The subject is generally known to have been exposed to the contact allergen. The subject may have a genetic or acquired disposition to allergy.

T-Cells

Generally the T cells which are provided for use in a method of the invention are taken from the subject in a blood sample, although other types of samples which contain T cells can be used. The sample may be added directly to the assay or may be processed first. Typically the processing may comprise diluting of the sample; for example with water or buffer. Typically the sample is diluted from 1.5 to 100 fold, for example 2 to 50 or 5 to 10 fold.

The processing may comprise separation of components of blood or other sample. Typically samples of mononuclear cells (MCs) or peripheral blood mononuclear cells (PBMCs) are prepared. The MCs will comprise the T cells and antigen presenting cells (APCs). Thus in the method the APCs present in the separated MCs can present a peptide which has been modified by the contact allergen to the T cells. In another embodiment only T cells, such as only CD4 or only CD8 T cells, are purified from the sample. PBMCs, MCs and T cells can be separated from the sample using techniques known in the art, such as those described in Lalvani et al (1997) *J. Exp. Med.* 186, p 859-865.

Preferably the T cells used in the assay are in the form of unprocessed or diluted samples, or are freshly isolated T cells (such as in the form of freshly isolated MCs or PBMCs) which are used directly ex vivo, i.e. they are not cultured before being used in the method. Typically $10^5$ to $10^7$, preferably $5 \times 10^5$ to $5 \times 10^6$, more preferably $2 \times 10^5$ to $2 \times 10^5$ PBMCs are added to each assay.

The APC may be a naturally occurring APC or an artificial APC. The APC is a cell which is capable of presenting the peptide to a T cell. It is typically a B cell, dendritic cell or macrophage. It is typically separated from the same sample as the T cell and is typically co-purified with the T cell. Thus the APC may be present in MCs or PBMCs. The APC is typically a freshly isolated ex vivo cell or a cultured cell. It may be in the form of a cell line, such as a short term or immortalised cell line. The APC may express empty MHC class II molecules on its surface.

Cytokines

A T cell which is sensitive to the allergen responsible for the allergy being diagnosed typically releases one or more cytokine when the T cell is contacted with the allergen. Any cytokine released by the T cell in response to the allergen may be detected in a method of the invention. Preferably the cytokine is released from a helper (Th2) T cell. More preferably the cytokine detected in a method of the invention is selected from IL-2, IL-4, IL-5, IL-13 and IFN-γ. A method of the invention may detect one, two, three or more cytokines simultaneously or sequentially. More than one assay each designed to detect a different cytokine may be performed to diagnose an allergy. Preferably, where detection of two or more cytokines is required, the cytokines are detected using a single assay.

Antibodies

Any agent which is capable of specifically binding to the substance secreted, by T cells in response to an allergen may be used to detect release of the substance from T cells. An agent "specifically binds" to a substance when it binds with preferential or high affinity to the substance for which it is specific but does not bind, does not substantially bind or binds with only low affinity to other substances. An agent capable of specifically binding to a substance is typically an antibody, such as a monoclonal or a polyclonal antibody. Monoclonal antibodies are preferred for use in a method of the invention.

An antibody suitable for use in a method of the invention typically binds specifically to one or more cytokines, preferably to one cytokine. Preferably the antibody binds specifically to IL-2, IL-4, IL-5, IL-13 or IFN γ. A method of the invention may utilize one or more, for example 2 or 3, antibodies wherein each antibody specifically binds to a different cytokine. For example, antibodies to IL-2 and IL-4, IL-2 and IL-5, IL-2 and IL-13, IL-2 and IFN γ, IL-4 and IL-5, IL-4 and IL-13, IL-4 and IFN γ, IL-5 and IL-13, IL-5 and IFN γ or IL-13 and IFN γ may be used in a method of the invention. Antibodies to cytokines are commercially available, or can be made using standard techniques. Commercially available antibodies include the following monoclonal antibodies from Mabtech AB, Stockholm, Sweden: IL2-I and IL2-II for IL-2, 82.4 and 12.1 for IL-4 TRFK5 and 5A01 for IL-5, IL1 3-I IL13-II for IL-13 and 1-D1K and 7-B6-1 for IFN γ.

The specific binding agent is immobilised on a solid support. Any suitable solid support may be used, for example, a polyvinylidene difluoride membrane. The immobilised support may be a plate with wells, such as a microtitre plate. Separate assays can therefore be carried out in separate wells in the plate. Preferably the surface to which the specific binding agent is immobilised is the base of a well. An antibody may be bound to the support by contacting the support and the antibody under conditions suitable for the antibody to bind to the support and washing to remove unbound antibody.

Form in which Allergen Added to Assay

The allergen may be provided in any suitable form. Preferably the allergen is present in a liquid form, such as a solution. Any suitable solution of a metal salt containing may be used in an assay of the invention. Typically where the allergen is nickel, a solution of $NiCl_2$ or $NiSO_4$ may be used. Any suitable concentration of the salt may be used. Typically, the concentration of the cation salt is from 1 μM to 10 mM, for example, from 5 μM to 1 mM, from 10 μM to 100 μM, from 20 μM to 90 μM, from 30 μM to 80 μM, from 40 μM to 60 μM, preferably from 50 μM to 100 μM.

Suitable Assay Format

The T cells and allergen may be contacted under any conditions suitable for activation of the T cells by the allergen. A T cell is activated by an allergen when the presence of the allergen stimulates the T-cell to produce a cytokine such as IL-4, IL-5 and/or IL-13. The conditions may also be suitable for the substance to interact directly with an immobilised specific binding agent. Generally the T cells will be present in a liquid sample which is in contact with the surface to which the binding agent has been immobilised. The allergen may be added to the sample of T cells in contact with the surface. Alternatively, the allergen may be present in a solution which is in contact with the surface to which the binding agent has been immobilised and the T cells may be added to the allergen. The allergen may be immobilised to a surface, such as the surface to which the specific binding agent is immobilised. T cells may then be brought into contact with the allergen and the specific binding agent simultaneously.

The assay may be carried out in any suitable volume. Generally the equal volumes of the T cell sample and the solution of allergen are used. Typical volumes of the T-cell sample range from 10 µl to 1 ml, preferably from 50 µl to 500 µl, more preferably from 100 µl to 200 µl.

Typically the length of time for which the T cells are incubated with the allergen and specific binding agent is from 4 to 50 hours, for example for 48 hours, from 8 to 45 hours, from 12 to 36 hours or from 16 to 24 hours, preferably 6 to 16 hours. Typically the T-cells, antigen and specific binding agent are incubated overnight.

The T cells may be incubated with the allergen and specific binding agent at any suitable temperature. A suitable temperature is in the same range as the normal body temperature of the human or animal from which the T cells are derived. Typically the incubation is carried out at a temperature between 35° C. and 39° C., preferably from 36° C. to 38° C., more preferably at 37° C.

Detection of Antibody/Cytokine Complex

The complex formed between the immobilised specific binding agent and the cytokine released from the T cells in response to the allergen may be detected by any suitable means. After binding the agent the cytokine will remain in the vicinity of the T cell which secreted it. Thus 'spots' of cytokine/agent complex are formed on the support, each spot representing a T cell which is secreting the cytokine. Quantifying the spots, and typically comparing against a control, allows determination of recognition of the allergen. The surface to which the specific binding agent is immobilised is generally washed, for example in PBS, to remove unbound cytokine.

Typically the agent/cytokine, for example the antibody/cytokine, complex may be detected using a second binding agent which will bind the complex. The second binding agent is typically a different agent to the first specific binding agent. Typically the second binding agent binds the cytokine at a site which is different from the site which binds the first agent. The second agent may bind to the complex formed between the cytokine and the first binding agent immobilised on the solid support. Preferably the second binding agent is an antibody. More preferably, the second binding agent is an antibody that specifically binds to the cytokine. The second binding agent is typically capable of binding to the cytokine when the cytokine is bound to the first binding agent. Thus the first and second binding agents typically bind to different parts of the cytokine molecule.

Generally the second binding agent is labelled with a label that may be detected either directly or indirectly. A specific binding agent comprising a directly detectable label may comprise a fluorescent label such as fluoroscein, texas red, rhodamine or oregon green. The binding of the second fluorescently labelled agent to immobilised first agent/substance complexes may be detected by microscopy. For example, using a fluorescence or confocal microscope.

A second binding agent comprising an indirectly detectable label may be detected by a third agent which is labelled directly or indirectly by a detectable label. The third agent will typically bind to the label on the second agent. For example the second agent may preferably comprise a biotin moiety, allowing detection by a third agent which comprises a streptavidin moiety and typically alkaline phosphatase as the detectable label.

The second binding agent may comprise an enzyme which acts on a precipitating non-fluorescent substrate that can be detected under a conventional low magnifying, for example 10× magnification, 20× magnification or 50× magnification, microscope such as a stereomicroscope. Preferably the precipitating non-fluorescent-substrate is detected using an automated ELISpot reader. An automated ELISpot reader is typically based on a video camera and image analysis software adapted from the analysis of spots.

The second specific binding agent may be an antibody from a different species to both the first antibody and the subject from which the T cells are taken. The third binding agent may then be an antibody that specifically recognises proteins from the species from which the second antibody is derived.

In all detection steps it is desirable to include an agent to minimise non-specific binding of the second and subsequent agents. For example bovine serum albumin (BSA) or fetal calf serum (FCS) may be used to block non-specific binding.

In one embodiment the allergen is $Ni^{2+}$ which stimulates T cells from an allergic subject to produce interleukin-4 (IL-4). IL-4 secreted from the T cell is bound by a first IL-4 antibody which is immobilised on a solid support. The bound IL-4 is then detected using a second IL-4 antibody which is labelled with a detectable label. The first and second IL-4 antibodies binds to different regions of the IL-4 molecule such that binding of IL-4 to the first antibody does not impair binding of IL-4 to the second antibody.

The cytokine released from T cells in response to the allergen may also be released spontaneously from T cells in the absence of the allergen. Therefore, it may be necessary to carry out one or more negative control assay to determine whether one or more T cells are releasing the cytokine in response to the allergen. For example, the assay may be carried out in the absence of the allergen and the number of "spots" detected in the absence of allergen may be subtracted from the number of "spots" (positive T cells) detected in the presence of allergen. Typically, from 0 to 10 cells per $2\times10^5$ cells may release the substance in the absence of the allergen.

Allergic Subject

A subject may be diagnosed as having an allergy to a specific allergen if the number of positive T cells detected in the presence of allergen is greater than the number of positive T cells detected in the absence of allergen. Typically, in the presence of allergen at least 5, preferably at least 7, at least 10, at least 15, at least 20, at least 30, at least 40, at least 50 or at least 100 more cells per $2\times10^5$ cells will release the cytokine compared to cells from the same subject in the absence of allergen.

Kits

The invention also provides a kit for carrying out the method comprising comprises an allergen, a surface comprising an immobilised agent capable of specifically binding to a cytokine released from T cells in response to the allergen and optionally a means to detect binding of said agent to said cytokine.

The kit may include a means for contacting the allergen and the surface with a T cell sample. Such means may be any suitable receptacle, for example a single well or a well of a microtitre plate.

The kit may also comprise a means to detect the cytokine/agent complex. A detectable change may occur in the agent itself after binding the cytokine, such as a colour change. Alternatively a second agent directly or indirectly labelled for detection may be allowed to bind the cytokine/agent complex to allow the determination of the spots. As discussed above the second agent may be specific for the cytokine, but binds a different site on the substance than the first agent.

The surface to which the specific binding agent is attached may be a surface of a well, preferably the base of the well. Typically the well is present in a plate with wells, such as a microtitre plate. Each assay can therefore be carried out in a separate well in the plate.

The kit may additionally comprise medium for the T cells, detection agents or washing buffers to be used in the detection steps. The kit may additionally comprise reagents suitable for the separation from the sample, such as the separation of PBMCs or T cells from the sample. The kit may be designed to allow detection of the T cells directly in the sample without requiring any-separation of the components of the sample.

The kit may also comprise controls, such as positive or negative controls. The positive control may allow the detection system to be tested. Thus the positive control typically mimics recognition of the allergen in any of the above methods. Typically in the kits designed to determine recognition in vitro the positive control is a cytokine, such as IL-2, IL-4, IL-5, IL-13 or IFN γ. Alternatively, the positive control may comprise a means for analysing polyclonally stimulated T-cells. For example, such means may comprise phytohemagglutinin (PHA) or anti-CD3 for stimulating T-cells.

The kit may also comprise a means to take a sample containing T cells from the host, such as a blood sample. The kit may comprise a means to separate mononuclear cells or T cells from a sample from the host.

EXAMPLES

Example 1

Selection of Patient and Control Subjects for Nickel-Allergy Testing

All individuals defined as nickel-induced allergic contact dermatitis (ACD) patients were selected based on previous history of ACD (n=11; age range 28-52; all female). Control individuals did not have a previously recorded problem with ACD (n=9; age range 40-54; all female). All individuals participated in the study after informed consent had been obtained and the project had been reviewed and accepted by the local ethic committee.

To confirm that the group of non-allergic controls did not include and potentially allergic individuals and that the patients were allergic to nickel, all individuals were patch tested. Prior to the patch testing of the control group, blood samples for ELISpot analysis were taken to avoid an impact of the patch test on the ELISpot analysis. Epicutaneous patch tests using 5% $NiSO_4$ in petrolatum was applied for 48 h whereafter the reaction, sites were inspected. None of the controls responded positively. All ACD patients were selected based on previous patch tests giving scores of 2+ or 3+ having 3+ as the highest score. The results of the patch tests are shown in Table 1.

TABLE 1

IL-4 ELISpot responses to $NiCl_2$ in nickel-allergic and non-allergic individuals

| Group | Subject | Age | Sex | Patch test reactivity | Total IgE (kU/1) | Proliferation (SI) (50 µM $NiCl_2$) | IL-4 producing cells/200 000 PBMC after stimulation with 0, 50 or 100 µM $NiCl_2$ | | | | |
|---|---|---|---|---|---|---|---|---|---|---|---|
| | | | | | | | 0 | 50 | 100 | 50-0 | 100-0 |
| Allergic | MU | 48 | F | +++ | 9.3 | 15.9 | 3 | 137 | nd | 134 | nd |
| | CT | 35 | F | ++ | .2 | 8.4 | 1 | 48 | nd | 47 | nd |
| | PL | 41 | F | ++ | 4.0 | 15.4 | 2 | 19 | 21 | 17 | 19 |
| | EE | 29 | F | +++ | 48 | 16.2 | 5 | 26 | 28 | 21 | 23 |
| | NH | — | F | +++ | 47 | 11.8 | 9 | 127 | 122 | 118 | 113 |
| | SJ | 28 | F | ++ | 3.4 | 24.9 | 2 | 27 | 30 | 25 | 28 |
| | SH | 52 | F | ++ | 8.6 | 11.0 | 5 | 60 | 63 | 55 | 58 |
| | KE | 35 | F | ++ | 3.5 | 31.6 | 4 | 9 | 16 | 5 | 12 |
| | VL | 45 | F | ++ | 90 | 44.8 | 1 | 8 | 18 | 7 | 17 |
| | MG | 41 | F | ++ | 32 | 10.1 | 1 | 13 | 24 | 12 | 23 |
| | MF | 35 | F | ++ | 46 | 92.2 | 3 | 23 | 28 | 21 | 25 |
| Non-allergic | GG | 42 | F | − | 13 | 3.1 | 2 | 3 | nd | 1 | nd |
| | IE | 53 | F | − | 63 | 0.9 | 2 | 4 | 5 | 2 | 3 |
| | BW | 51 | F | − | 8.5 | 3.1 | 5 | 9 | 8 | 4 | 3 |
| | AKA | 54 | F | − | 19 | 1.2 | 3 | 3 | 4 | 0 | 1 |
| | CO | 40 | F | − | 19 | 2.0 | 9 | 7 | 14 | 0 | 5 |
| | CJ | 43 | F | − | 22 | 3.3 | 2 | 1 | 4 | 0 | 2 |
| | EJ | 46 | F | − | 2.0 | 6.8 | 2 | 2 | 1 | 0 | 0 |
| | LL | — | F | − | 37 | 5.1 | 4 | 4 | 8 | 0 | 4 |
| | MBH | 49 | F | − | 8.4 | 8.2 | 5 | 2 | 6 | 0 | 1 |

Example 2

Separation of Peripheral Blood Mononuclear Cells

Blood from ACD patients or control individuals were obtained by venipuncture and collected in sterile heparinised glass vials. Peripheral blood mononuclear cells (PBMC) were separated by density gradient centrifugation over Ficoll-Hypaque. After separation, PBMC were washed twice in medium (RPMI 1640 containing glutamin, Hepes, Penicillin/Streptomycin and 10% fetal calf serum (FCS)) and used fresh for experiments. Alternatively, PBMC were frozen in 90% FCS and 10% dimethylsulfoxide and kept in liquid nitrogen until tested. Prior to being tested, frozen cells were thawed at 37° C. and medium was added dropwise whereafter the cells were washed twice with medium. Comparison of the use of fresh and frozen cells in ELISpot with regard to cytokine responses to $NiCl_2$ or other stimuli resulted in comparable number of spots.

Example 3

Stimulation of PBMC

The PBMC were stimulated with various concentrations of $NiCl_2$ and both proliferative responses and cytokine responses were analysed. $NiCl_2$ at a stock concentration of 50 mM was mixed with medium and incubated for more than five minutes before being added to cells. PBMC diluted to a cell concentration of $4-6 \times 10^6$ cells/ml were mixed with an equal volume of $NiCl_2$ diluted in medium resulting in a final concentration of $2 \times 10^6$ cells/ml and $NiCl_2$ at concentrations ranging from 10-100 µM. The cell suspensions were incubated in plastic vials for 4 h at 37° C. in a humidified incubator. In parallel with incubating PBMC with $NiCl_2$, PBMC at the same concentration were incubated with mitogen (1 µg phytohemagglutinin (PHA)/ml), control antigens (10 µg tetanus toxoid (TT) or purified protein derivative (PPD)/ml) or in the absence of stimuli. Comparison of ELISpot cytokine responses induced by $NiCl_2$ and $NiSO_4$ in a limited number of individuals resulted in similar responses.

Proliferative responses are displayed in Table 1 as stimulation indices (SEQ ID NO.) corresponding to the cpm values obtained by stimulation of PBMC with 50 µM $NiCl_2$ divided by the proliferation of cells in the absence of stimuli.

The mean proliferative responses to 50 µM $NiCl_2$ were higher in the group of allergic individuals (Table 1) and the difference was statistically significant (Mann-Whitney; p<0.0002). However, there was little difference between the lowest responders in the allergic group and the highest responders in the non-allergic group.

Example 4

ELISpot Assay

Matched pairs of monoclonal antibodies (mAb) to human IL-4, IL-5 or IL-13 were used for the ELISpot assays (Mabtech AB, Stockholm, Sweden). For each pair, one mAb was used as a capture mAb: 82.4 (IL-4), TRFK5 (IL-5) and IL13-I (IL-13) and the other for detection, 12.1 (IL-4), 5A10 (IL-5) and IL13-II (IL-13). MAbs used for detection were biotinylated.

Ninetysix-well plates with polyvinylidene difluoride membranes (MAIPS45-10, Millipore) were treated with 100 µl of 70% EtOH for 2-10 min followed by six washes with 200 µl sterile deionized $H_2O$. To each well, 100 µl of capture mAb at a concentration of 15 µg/ml in phosphate-buffered saline (PBS) was added and incubated over night at +4° C. The plates were washed three times with 200 µl or sterile PBS and three times with 200 µl medium containing 2% FCS. PBMC incubated for 4 h with or without stimuli in test tubes were suspended and 100 µl cell suspension ($2 \times 10^5$ cells) was added to each well. After an additional incubation of 44 h, the wells were emptied and washed six times with 200 µl PBS. Biotinylated detection mAb at 1 µg/ml in PBS containing 0.5% FCS was added at a volume of 100 µl and incubated for 2 h at room temperature whereafter the wells were washed six times with PBS. Subsequently, 100 µl of SA-ALP (Streptavidin-Alkaline phosphatase, Mabtech) at 50 ng/ml in PBS with 0.5% FCS was added to each well and incubated for 1 h followed by washing in PBS six times before developing the wells with 100 µl nitroblue tetraxolium (NBT)/5-bromo-4-chloro-3-indolyl phosphate (BCIP) substrate (Sigma) for approximately 1 h. After rinsing the plates with tap water, the plates were dried and spots were counted using a light microscope.

Measurements of PBMC responses to $NiCl_2$ by ELISpot were performed to enumerate the number of cells producing IL-4 (Table 1). A low frequency of cells producing IL-4 spontaneously was observed in both groups, 1-9 spots/200 000 cells in the allergic group and 2-9 spots/200 000 cells in the non-allergic group. In contrast, the number of cells producing IL-4 in response to $NiCl_2$ was increased in the allergic group whereas no such increase was seen in the control group. When comparing the number of $NiCl_2$-induced spots in the two groups, after subtraction of the spontaneous spots, the number of spots were higher in all allergic individuals (Table 1, last two columns). This was seen using either 50 µM or 100 µM of $NiCl_2$ and although the difference was more evident at the higher concentration, the increase was statistically significant in both cases (Mann-Whitney p<0.0002 at 50 mM and p<0:0005 at 100 mM). Stimulation with 10 µM of $NiCl_2$ also resulted in higher mean values for the allergic group although the difference between the groups was small (data not shown).

To compare the number of cells from the two groups producing other cytokines in response to $NiCl_2$, PBMC from some of the individuals were also analysed for IL-5 and IL-13 in the ELISpot (FIG. 1). Similar to the IL-4 response, PBMC from allergic individuals (n=8) were shown to produce IL-5 and IL-13 in response to $NiCl_2$ whereas this was not seen in non-allergic individuals (n=7). As the case of IL-4, a very low number of cells from either group was found to produce IL-5 spontaneously. The spontaneous production of IL-13 was slightly higher but did not differ significantly between the two groups. When comparing the number of $NiCl_2$-induced IL-4, IL-5 and IL-13 spots in the two groups, the response of the allergic group was higher for all three cytokines (Mann-Whitney; p=0.0032, p=0.0018 and p=0.0038, respectively). There was also a clear association between the number of IL-4 and IL-5 spots as well as the number of IL-4 and IL-13 spots (data not shown).

Example 5

Measurement of Total IgE Levels in Plasma

Plasma from all individuals participating in the study were analysed for total IgE content. The test used was a commercially available assay and it was performed according to the instructions of the manufacturer. Total IgE plasma levels (Table 1) were similar in both the test groups and ranged from 2-90 kU/l in the allergic group and 2-63 kU/l in the non-allergic group. This suggest that cytokine responses to $NiCl_2$ are allergen specific and does not reflect a generally biased TH2 type of mitogenic activiation.

Example 6

Kathon (Methylisothiazolinone) Allergy Testing

Individuals defined as allergic to the preservative compound Kathon (methylisothiazolinone) were selected. Control individuals did not have a previously recorded problem with Kathon (methylisothiazolinone) allergy. All individuals participated in the study after informed consent had been obtained and the project had been reviewed and accepted by the local ethic committee.

Peripheral blood mononuclear cells (PBMC) were obtained from Kathon (methylisothiazolinone) allergy patients or control individuals as described in Example 2.

The PBMC were stimulated with Kathon (methylisothiazolinone) and cytokine responses were analysed.

Matched pairs of monoclonal antibodies (mAb) to human IL-4, IL-5, IL-13 or IFN-γ were used for ELISpot assays (Mabtech AB, Stockholm, Sweden). As in Example 4 above, for each pair, one mAb was used as a capture mAb and the other for detection. MAbs used for detection were biotinylated.

Ninetysix-well plates with polyvinylidene difluoride membranes (MAIPS45-10, Millipore) were treated with 100 μl of 70% EtOH for 2-10 min followed by six washes with 200 μl sterile deionized H$_2$O. To each well, 100 μl of capture mAb at a concentration of 15 μg/ml in phosphate-buffered saline (PBS) was added and incubated over night at +4° C. The plates were washed three times with 200 μl or sterile PBS and three times with 200 μl medium containing 2% FCS. PBMC incubated for 4 h with or without stimuli in test tubes were suspended and 100 μl cell suspension (2×10$^5$ cells) was added to each well. After an additional incubation of 44 h, the wells were emptied and washed six times with 200 μl PBS. Biotinylated detection mab at 1 μg/ml in PBS containing 0.5% FCS was added at a volume of 100 μl and incubated for 2 h at room temperature whereafter the wells were washed six times with PBS. Subsequently, 100 μl of SA-ALP (Streptavidin-Alkaline phosphatase, Mabtech) at 50 ng/ml in PBS with 0.5% FCS was added to each well and incubated for 1 h followed by washing in PBS six times before developing the wells with 100 μl nitroblue tetraxolium (NBT)/5-bromo-4-chloro-3-indolyl phosphate (BCIP) substrate (Sigma) for approximately 1 h. After rinsing the plates with tap water, the plates were dried and spots were counted using a light microscope.

Measurements of PBMC responses to Kathon (methylisothiazolinone) by ELISpot were performed to enumerate the number of cells producing IL-4, IL-5, IL-13 and IFN-γ (Table 2).

Table 2. ELISpot Test of Individuals Allergic to Kathon (Methylisothiazolinone) and of Non Allergic Individuals

TABLE 2

| ELISpot test of individuals allergic to Kathon (methylisothiazolinone) and of non allergic individuals | | | | |
|---|---|---|---|---|
| | Number of responding cells (spots) per 200,000 cells | | | |
| | IL-4 | IL-5 | IL-13 | IFN-gamma |
| Allergic Individuals | | | | |
| Patient 1 | 14 | 3 | 51 | 39 |
| Patient 2 | 21 | 5 | 50 | 113 |
| Patent 3* | 0 | 0 | 0 | 0 |
| Patient 4 | 3 | 2 | 19 | 21 |
| Non-allergic controls | | | | |
| Control 1 | 0 | 0 | 0 | 4 |
| Control 2 | 0 | 0 | 0 | 0 |
| Control 3 | 0 | 0 | 0 | 0 |
| Control 4 | 1 | 0 | 0 | ND |

*Patient 3 was selected to be allergic but was tested negative in patch test.

The data in table 2 represents the number of cells specifically responding to Kathon (methylisothiazolinone). Thus, if any spontaneous spots (i.e. without stimuli) were seen, these were subtracted. In the case of IL-4, IL-5 and IL-13, the numbers of such spontaneous spots were consistently low, whereas spontaneous production of IFN γ showed a greater individual variation.

To confirm that the group of non-allergic controls did not include any potentially allergic individuals and that the patients were allergic to Kathon (methylisothiazolinone), all individuals were patch tested. Prior to the patch testing of the control group, blood samples for ELISpot analysis were taken to avoid an impact of the patch test on the ELISpot analysis. Epicutaneous patch tests were applied for 48 h whereafter the reaction sites were inspected. None of the controls responded positively. Patients 1, 2 and 4 responded positively in the patch test. Patient number 3 who was selected to be a Kathon (methylisothiazolinone) allergic was shown to be negative in the patch test. This patient also gave a negative result in the ELISpot assay (see Table 2).

The invention claimed is:

1. An in vitro method for diagnosing a nickel allergy in a subject, which method comprises:
    (i) providing
        (a) a solution comprising a nickel salt;
        (b) T-cells from said subject;
        (c) antigen presenting cells; and
        (d) a surface to which is immobilized a first antibody capable of specifically binding to a cytokine released from said T-cells in response to said nickel salt wherein said cytokine is selected from the group consisting of IL-4, IL-5, and IL-13;
    (ii) contacting said T-cells with said nickel salt, said antigen presenting cells and said surface under conditions which are suitable for
        (a) release of said cytokine by said T-cells that have been presensitized in vivo to nickel by skin contact of the subject with said nickel; and
        (b) binding of said cytokine to said first antibody to form a cytokine/antibody complex; and
    (iii) detecting binding of said cytokine to said first antibody, by enumerating spots of said cytokine/antibody complex formed on the surface, where each spot represents a T-cell which is secreting said cytokine, thereby detecting any nickel-specific T-cells at the single cell level which have been presensitized by skin contact of the subject with said nickel, where the detection of said presensitized T-cells secreting IL-4, IL-5, IL-13 or a combination thereof, correlates with said nickel allergy.

2. A method according to claim 1 wherein said nickel salt is a solution of NiCl$_2$ or NiSO$_4$.

3. A method according to claim 1 wherein said spots are detected using a second antibody which specifically binds to said cytokine.

4. A method according to claim 3 wherein said second antibody is labeled.

5. A method according to claim 1 wherein said T-cells which are secreting two or more of said cytokines are detected.

6. An in vitro method for diagnosing a skin contact allergy to nickel in a subject, which method comprises:
   (i) providing
      (a) a solution comprising a nickel salt;
      (b) T-cells from said subject;
      (c) antigen presenting cells; and
      (d) a surface to which is immobilized a first antibody capable of specifically binding to a cytokine released from said T-cells in response to said nickel salt, wherein said cytokine is selected from the group consisting of IL-4, IL-5, and IL-13;
   (ii) contacting said T-cells with said solution, said antigen presenting cells and said surface under conditions which are suitable for
      (a) release of said cytokine by said T-cells that have been presensitized in vivo to said nickel by skin contact of the subject with the said nickel; and
      (b) binding of said cytokine to said first antibody to form a cytokine/antibody complex; and
   (iii) detecting binding of said cytokine to said first antibody by enumerating spots of said cytokine/antibody complex formed on the surface, where each spot represents a T-cell which is secreting said cytokine, thereby detecting nickel-specific T-cells at the single cell level which have been presensitized by skin contact of the subject with said nickel, where the detection of the presensitized T-cells secreting IL-4, IL-5, IL-13, or a combination thereof, correlates with said contact allergy to nickel.

7. An in vitro method for diagnosing nickel allergy in a subject, which method comprises:
   (i) providing
      (a) a nickel salt;
      (b) T-cells from said subject;
      (c) antigen presenting cells; and
      (d) a surface to which is immobilized a first antibody capable of specifically binding to a cytokine released from said T-cells in response to said nickel salt, wherein said cytokine is selected from the group consisting of IL-4, IL-5 and IL-13;
   (ii) contacting said T-cells with said nickel salt, said antigen presenting cells and said surface under conditions which are suitable for
      (a) release of said cytokine by said T-cells that have been presensitized in vivo to nickel and
      (b) binding of said cytokine to said first antibody to form a cytokine/antibody complex; and
   (iii) detecting binding of said cytokine to said first antibody, by enumerating spots of said cytokine/antibody complex formed on the surface, where each spot represents a T-cell which is secreting said cytokine, thereby detecting nickel-specific T-cells at the single cell level, where said spots are enumerated using a second antibody which is labeled and which specifically binds to said cytokine and where the detection of the presensitized T-cells secreting IL-4, IL-5, IL-13, or a combination thereof, correlates with said nickel allergy.

8. An in vitro method for determining whether a subject has an allergy against nickel, where the allergy is caused by contact of the skin of said subject with said nickel, which method comprises:
   (i) providing
      (a) a solution comprising said nickel;
      (b) T-cells from said subject;
      (c) antigen presenting cells; and
      (d) a surface to which is immobilized a first antibody capable of specifically binding to a cytokine released from said T-cells in response to said nickel wherein said cytokine is selected from the group consisting of IL-4, IL-5, and IL-13;
   (ii) contacting said T-cells with said nickel, said antigen presenting cells and said surface under conditions which are suitable for:
      (a) release of said cytokine by said T-cells that have been presensitized in vivo to said nickel; and
      (b) binding of said cytokine to said first antibody to form a cytokine/antibody complex;
   (iii) detecting binding of said cytokine to said first antibody by enumerating spots of said cytokine/antibody complex formed on the surface, where each spot represents a T-cell which is secreting said cytokine, thereby detecting cytokine releasing T-cells at the single cell level; and
   (iv) comparing the results of (iii) with those of a control performed without said nickel, where if the number of said cytokine releasing T-cells is greater in (iii) than for the control, the subject is determined to have an allergy against nickel.

9. An in vitro method for determining whether a subject has an allergy against nickel, where the allergy is caused by contact of the skin of said subject with said nickel, said method being carried out in a microtitre plate, with assays using an antibody against different cytokines being performed in separate wells of said microtitre plate, where:
   (i) for each assay providing in a well of said microtitre plate
      (a) a solution comprising said nickel;
      (b) T-cells from said subject;
      (c) antigen presenting cells; and
      (d) a surface to which is immobilized a first antibody capable of specifically binding to a cytokine released from said T-cells in response to said nickel wherein said cytokine is selected from the group consisting of IL-4, IL-5, and IL-13;
   (ii) for each assay contacting said T-cells with said nickel, said antigen presenting cells and said surface under conditions which are suitable for
      (a) release of said cytokine by said T-cells that have been presensitized in vivo to said nickel; and
      (b) binding of said cytokine to said first antibody to form a cytokine/antibody complex;
   (iii) for each assay detecting binding of said cytokine to said first antibody by enumerating spots of said cytokine/antibody complex formed on the surface, where each spot represents a T-cell which is secreting said cytokine, thereby detecting cytokine release by said T-cells at the specific T-cell level and hence whether said subject has said allergy against nickel, where said spots are enumerated using a second antibody which is labeled and which specifically binds to said cytokine; and
   (iv) comparing the results of (iii) with those of a control performed without said nickel, where if the number of cytokine releasing T-cells is greater in (iii) than for the control for at least one said cytokine, the subject is determined to have an allergy against nickel.

10. A method according to claim 1, where the surface is a polyvinylidene difluoride membrane.

11. A method according to claim 6, where the surface is a polyvinylidene difluoride membrane.

12. A method according to claim 7, where the surface is a polyvinylidene difluoride membrane.

13. A method according to claim 8, where the surface is a polyvinylidene difluoride membrane.

14. A method according to claim 9, where the surface is a polyvinylidene difluoride membrane.

15. An in vitro method for diagnosing an allergy, where the allergy is caused by contact of the skin of a subject with nickel, which method comprises:
(i) providing
   (a) a $NiCl_2$ solution;
   (b) T-cells from said subject;
   (c) antigen presenting cells; and
   (d) a surface to which is immobilized a first antibody capable of specifically binding to a cytokine released from said T-cells in response to said $NiCl_2$ solution wherein said cytokine is selected from the group consisting of IL-4, IL-5, and IL-13;
(ii) contacting said T-cells with said $NiCl_2$ solution, said antigen presenting cells and said surface under conditions which are suitable for
   (a) release of said cytokine by said T-cells that have been presensitized in vivo to said nickel; and
   (b) binding of said cytokine to said first antibody, to form a cytokine/antibody complex; and
(iii) detecting binding of said cytokine to said first antibody by enumerating spots of said cytokine/antibody complex formed on the surface, where each spot represents a T-cell which is secreting said cytokine, said detection performed by using a labeled second antibody which binds to a cytokine selected from the group consisting of IL-4, IL-5 and IL-13 and quantifying spots of said cytokine/antibody complex, thereby detecting any nickel-specific T-cells at the single cell level and hence allergy caused by the contact of the skin to nickel.

16. An in vitro method for diagnosing nickel allergy in a subject, which method comprises:
(i) providing
   (a) $NiCl_2$;
   (b) T-cells from said subject;
   (c) antigen presenting cells; and
   (d) a surface to which is immobilized a first antibody capable of specifically binding to a cytokine released from said T-cells in response to $NiCl_2$, wherein said cytokine is selected from the group consisting of IL-4, IL-5 and IL-13;
(ii) contacting said T-cells with said $NiCl_2$, said antigen presenting cells and said surface under conditions which are suitable for
   (a) release of said cytokine by T-cells that have been presensitized in vivo to nickel by contact with the skin; and
   (b) binding of said cytokine to said first antibody to form a cytokine/antibody complex;
(iii) detecting binding of said cytokine to said first antibody by enumerating spots of said cytokine/antibody complex formed on the surface, where each spot represents a T-cell which is secreting the cytokine, said detection performed by using a labeled second antibody which binds to a cytokine selected from the group consisting of IL-4, IL-5 and IL-13 and quantifying spots of said cytokine/antibody complex, thereby detecting nickel-specific T-cells at the single cell level; and
(iv) comparing the results of (iii) with those of a control performed without said $NiCl_2$, where if the number of cytokine releasing T-cells is greater in (iii) than for the control for at least one said cytokine, the subject is determined to have an allergy to said nickel.

17. A method according to claim 1 wherein said T-cells from said subject and said antigen presenting cells are provided in the form of a sample of peripheral blood mononuclear cells (PBMCs) from said subject.

18. A method according to claim 6 wherein said T-cells from said subject and said antigen presenting cells are provided in the form of a sample of peripheral blood mononuclear cells (PBMCs) from said subject.

19. A method according to claim 7 wherein said T-cells from said subject and said antigen presenting cells are provided in the form of a sample of peripheral blood mononuclear cells (PBMCs) from said subject.

20. A method according to claim 8 wherein said T-cells from said subject and said antigen presenting cells are provided in the form of a sample of peripheral blood mononuclear cells (PBMCs) from said subject.

21. A method according to claim 9 wherein said T-cells from said subject and said antigen presenting cells are provided in the form of a sample of peripheral blood mononuclear cells (PBMCs) from said subject.

22. A method according to claim 15 wherein said T-cells from said subject and said antigen presenting cells are provided in the form of a sample of peripheral blood mononuclear cells (PBMCs) from said subject.

23. A method according to claim 16 wherein said T-cells from said subject and said antigen presenting cells are provided in the form of a sample of peripheral blood mononuclear cells (PBMCs) from said subject.

* * * * *

UNITED STATES PATENT AND TRADEMARK OFFICE
CERTIFICATE OF CORRECTION

| | | |
|---|---|---|
| PATENT NO. | : 8,278,054 B2 | Page 1 of 1 |
| APPLICATION NO. | : 10/471479 | |
| DATED | : October 2, 2012 | |
| INVENTOR(S) | : Jakobson | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 674 days.

Signed and Sealed this
Twenty-fourth Day of June, 2014

Michelle K. Lee
*Deputy Director of the United States Patent and Trademark Office*